(12) United States Patent
Edwards et al.

(10) Patent No.: US 8,412,318 B2
(45) Date of Patent: *Apr. 2, 2013

(54) TREATMENT OF TISSUE IN SPHINCTERS, SINUSES, AND ORIFICES

(75) Inventors: Stuart D. Edwards, Corral De Tierra, CA (US); Simon W. H. Thomas, Danville, CA (US)

(73) Assignee: Novasys Medical, Inc., Newark, CA (US)

( * ) Notice: Subject to any disclaimer, the term of this patent is extended or adjusted under 35 U.S.C. 154(b) by 1462 days.

This patent is subject to a terminal disclaimer.

(21) Appl. No.: 11/207,677

(22) Filed: Aug. 18, 2005

(65) Prior Publication Data

US 2006/0058780 A1 Mar. 16, 2006

Related U.S. Application Data

(63) Continuation of application No. 09/356,110, filed on Jul. 16, 1999, now Pat. No. 7,022,105, which is a continuation-in-part of application No. 08/717,612, filed on Sep. 20, 1996, now Pat. No. 6,077,257.

(51) Int. Cl.
*A61N 1/30* (2006.01)

(52) U.S. Cl. .................................. 604/21; 604/103.01

(58) Field of Classification Search .............. 604/21, 604/95.01–95.05, 96.01–103.14, 104–109, 604/523–532; 606/40; 607/101
See application file for complete search history.

(56) References Cited

U.S. PATENT DOCUMENTS

| | | | |
|---|---|---|---|
| 3,901,241 A | 8/1975 | Allen et al. | |
| 4,011,872 A | 3/1977 | Komiya | |
| 4,311,154 A | 1/1982 | Sterzer et al. | |
| 4,411,266 A | 10/1983 | Cosman | |
| 4,423,812 A | 1/1984 | Sato | |
| 4,532,924 A | 8/1985 | Auth et al. | |
| 4,565,200 A | 1/1986 | Cosman | |
| 4,674,506 A | 6/1987 | Alcond | |
| 4,832,688 A | 5/1989 | Sagae et al. | |
| 4,878,492 A | 11/1989 | Sinofsky et al. | |
| 4,901,737 A | 2/1990 | Toone | |
| 4,906,203 A | 3/1990 | Margrave | |
| 4,907,589 A | 3/1990 | Cosman | |
| 4,955,377 A | 9/1990 | Lennox et al. | |
| 4,966,597 A | 10/1990 | Cosman | |
| 4,976,711 A | 12/1990 | Parins | |

(Continued)

FOREIGN PATENT DOCUMENTS

| | | |
|---|---|---|
| EP | 0 139 607 | 5/1985 |
| EP | 0 608 609 | 8/1994 |

(Continued)

OTHER PUBLICATIONS

Rice, et al., "Total Endoscopic Sphenoethmoidectomy, The Technique of Wigand", Chaper 6, Endoscopic Paranasal Sinus Surgery Raven Press, 1988, pp. 103-124.

(Continued)

*Primary Examiner* — Nicholas Lucchesi
*Assistant Examiner* — Gerald Landry, II
(74) *Attorney, Agent, or Firm* — Michael A. Glenn; Glenn Patent Group

(57) ABSTRACT

The invention comprises a method and apparatus for treatment of a body part. More particularly, a method and apparatus for heat treatment of tissue using a catheter inserted into a body part is described along with means for positioning the catheter and means for positioning a set of electrodes relative to a tissue sample for treatment. Still more particularly, radio frequency energy at about 400 to 500 kilohertz is used to provide heat for the tissue treatment.

18 Claims, 8 Drawing Sheets

U.S. PATENT DOCUMENTS

| | | | |
|---|---|---|---|
| 4,947,842 A | 1/1991 | Nakamura | |
| 4,994,033 A | 2/1991 | Shockey et al. | |
| 5,002,558 A | 3/1991 | Klein et al. | |
| 5,007,897 A | 4/1991 | Kalb et al. | |
| 5,035,696 A | 7/1991 | Rydell | |
| 5,046,512 A | 9/1991 | Murchie | |
| 5,049,132 A | 9/1991 | Shaffer et al. | |
| 5,057,107 A | 10/1991 | Parins | |
| 5,078,717 A | 1/1992 | Parins | |
| 5,083,565 A | 1/1992 | Parins | |
| 5,092,841 A | 3/1992 | Spears | |
| 5,094,233 A | 3/1992 | Brennan | |
| 5,100,423 A | 3/1992 | Fearnot | |
| 5,100,429 A | 3/1992 | Sinofsky et al. | |
| 5,102,390 A | 4/1992 | Crittenden et al. | |
| 5,106,360 A | 4/1992 | Ishiwara et al. | |
| 5,122,137 A | 6/1992 | Lennos | |
| 5,125,928 A | 6/1992 | Parins | |
| 5,188,596 A | 2/1993 | Condon et al. | |
| 5,190,540 A | 3/1993 | Lee | |
| 5,190,541 A | 3/1993 | Abele | |
| 5,197,963 A | 3/1993 | Parins | |
| 5,197,964 A | 3/1993 | Parins | |
| 5,199,951 A | 4/1993 | Spears | |
| 5,209,776 A | 5/1993 | Bass et al. | |
| 5,213,580 A | 5/1993 | Slepian et al. | |
| 5,215,103 A | 6/1993 | Desai | |
| 5,219,335 A | 6/1993 | Parodi et al. | |
| 5,239,982 A | 8/1993 | Trauthen | |
| 5,257,451 A | 11/1993 | Edwards | |
| 5,273,535 A | 12/1993 | Edwards et al. | |
| 5,275,162 A | 1/1994 | Edwards | |
| 5,277,201 A | 1/1994 | Stern | |
| 5,278,201 A | 1/1994 | Dunn et al. | |
| 5,281,217 A | 1/1994 | Edwards | |
| 5,281,218 A | 1/1994 | Imran | |
| 5,286,254 A | 2/1994 | Shapland et al. | |
| 5,290,286 A | 3/1994 | Parins | |
| 5,293,869 A | 3/1994 | Edwards | |
| 5,309,910 A | 5/1994 | Edwards | |
| 5,313,943 A | 5/1994 | Houser | |
| 5,314,466 A | 5/1994 | Stern | |
| 5,318,531 A | 6/1994 | Leone | |
| 5,322,503 A | 6/1994 | Desai | |
| 5,324,288 A | 6/1994 | Billings | |
| 5,328,467 A | 7/1994 | Edwards | |
| 5,328,471 A | 7/1994 | Slepian et al. | |
| 5,334,196 A | 8/1994 | Scott | |
| 5,334,201 A | 8/1994 | Cowan | |
| 5,336,222 A | 8/1994 | Durgin, Jr. | |
| 5,342,357 A | 8/1994 | Nardella et al. | |
| 5,363,861 A | 11/1994 | Edwards et al. | |
| 5,365,926 A | 11/1994 | Desai | |
| 5,366,490 A * | 11/1994 | Edwards et al. | 607/99 |
| 5,368,592 A | 11/1994 | Stern et al. | |
| 5,370,675 A | 12/1994 | Edwards et al. | |
| 5,370,678 A | 12/1994 | Edwards et al. | |
| 5,383,876 A | 1/1995 | Nardella | |
| 5,383,917 A | 1/1995 | Desai et al. | |
| 5,385,544 A | 1/1995 | Edwards et al. | |
| 5,397,339 A | 3/1995 | Desai | |
| 5,398,683 A | 3/1995 | Edwards et al. | |
| 5,401,272 A | 3/1995 | Perkins | |
| 5,403,311 A * | 4/1995 | Abele et al. | 606/49 |
| 5,405,322 A | 4/1995 | Lennox et al. | |
| 5,409,453 A | 4/1995 | Lundquist et al. | |
| 5,421,819 A | 6/1995 | Edwards et al. | |
| 5,423,744 A | 6/1995 | Gencheff et al. | |
| 5,423,808 A | 6/1995 | Edwards et al. | |
| 5,423,811 A | 6/1995 | Imran et al. | |
| 5,423,812 A | 6/1995 | Ellman et al. | |
| 5,433,739 A | 7/1995 | Sluijter et al. | |
| 5,435,805 A | 7/1995 | Edwards et al. | |
| 5,456,662 A | 10/1995 | Edwards et al. | |
| 5,456,682 A | 10/1995 | Edwards et al. | |
| 5,458,568 A | 10/1995 | Racchini et al. | |
| 5,458,596 A | 10/1995 | Lax et al. | |
| 5,458,597 A | 10/1995 | Edwards et al. | |
| 5,464,404 A | 11/1995 | Abela et al. | |
| 5,470,308 A | 11/1995 | Edwards et al. | |
| 5,470,309 A | 11/1995 | Edwards et al. | |
| 5,471,982 A | 12/1995 | Edwards et al. | |
| 5,472,441 A | 12/1995 | Edwards et al. | |
| 5,484,400 A | 1/1996 | Edwards et al. | |
| 5,486,161 A | 1/1996 | Lax et al. | |
| 5,496,271 A | 3/1996 | Burton et al. | |
| 5,498,238 A | 3/1996 | Shapland et al. | |
| 5,505,728 A | 4/1996 | Ellman et al. | |
| 5,505,730 A | 4/1996 | Edwards | |
| 5,507,743 A | 4/1996 | Edwards et al. | |
| 5,509,419 A | 4/1996 | Edwards et al. | |
| 5,514,130 A | 5/1996 | Baker | |
| 5,514,131 A | 5/1996 | Edwards et al. | |
| 5,520,684 A | 5/1996 | Imran | |
| 5,531,676 A | 7/1996 | Edwards et al. | |
| 5,531,677 A | 7/1996 | Lundquist et al. | |
| 5,536,240 A | 7/1996 | Edwards et al. | |
| 5,536,267 A | 7/1996 | Edwards et al. | |
| 5,540,655 A | 7/1996 | Edwards et al. | |
| 5,542,915 A | 8/1996 | Edwards et al. | |
| 5,545,161 A | 8/1996 | Imran | |
| 5,545,171 A | 8/1996 | Sharkey et al. | |
| 5,545,193 A | 8/1996 | Fleischman et al. | |
| 5,549,108 A | 8/1996 | Edwards et al. | |
| 5,549,644 A | 8/1996 | Lundquist et al. | |
| 5,554,110 A | 9/1996 | Edwards et al. | |
| 5,556,377 A | 9/1996 | Edwards et al. | |
| 5,558,672 A | 9/1996 | Edwards et al. | |
| 5,558,673 A | 9/1996 | Edwards et al. | |
| 5,569,241 A | 10/1996 | Edwards | |
| 5,569,242 A | 10/1996 | Lax et al. | |
| 5,575,788 A | 11/1996 | Baker et al. | |
| 5,582,589 A | 12/1996 | Edwards et al. | |
| 5,588,960 A | 12/1996 | Edwards et al. | |
| 5,591,125 A | 1/1997 | Edwards et al. | |
| 5,591,199 A | 1/1997 | Porter et al. | |
| 5,599,294 A | 2/1997 | Edwards et al. | |
| 5,599,295 A | 2/1997 | Rosen et al. | |
| 5,599,307 A | 2/1997 | Bacher et al. | |
| 5,599,345 A | 2/1997 | Edwards et al. | |
| 5,599,346 A | 2/1997 | Edwards et al. | |
| 5,601,591 A | 2/1997 | Edwards et al. | |
| 5,607,389 A | 3/1997 | Edwards et al. | |
| 5,609,151 A | 3/1997 | Muller et al. | |
| 5,624,439 A | 4/1997 | Edwards et al. | |
| 5,662,609 A | 9/1997 | Slepian | |
| 5,667,488 A | 9/1997 | Lundquist et al. | |
| 5,674,191 A | 10/1997 | Edwards et al. | |
| 5,681,277 A | 10/1997 | Edwards et al. | |
| 5,681,308 A | 10/1997 | Edwards et al. | |
| 5,683,384 A | 11/1997 | Gough et al. | |
| 5,685,839 A | 11/1997 | Edwards et al. | |
| 5,688,266 A | 11/1997 | Edwards et al. | |
| 5,697,281 A * | 12/1997 | Eggers et al. | 604/114 |
| 5,707,349 A | 1/1998 | Edwards | |
| 5,715,817 A * | 2/1998 | Stevens-Wright et al. | 600/373 |
| 5,718,702 A | 2/1998 | Edwards | |
| 5,720,718 A | 2/1998 | Rosen et al. | |
| 5,722,975 A | 3/1998 | Edwards et al. | |
| 5,728,094 A | 3/1998 | Edwards | |
| 5,728,144 A | 3/1998 | Edwards et al. | |
| 5,730,719 A | 3/1998 | Edwards | |
| 5,738,114 A | 4/1998 | Edwards | |
| 5,741,225 A | 4/1998 | Lax et al. | |
| 5,743,870 A | 4/1998 | Edwards | |
| 5,743,904 A | 4/1998 | Edwards | |
| 5,746,224 A | 5/1998 | Edwards | |
| 5,749,846 A | 5/1998 | Edwards et al. | |
| 5,762,626 A * | 6/1998 | Lundquist et al. | 604/22 |
| 5,769,846 A | 6/1998 | Edwards et al. | |
| 5,797,903 A * | 8/1998 | Swanson et al. | 606/34 |
| 5,800,484 A | 9/1998 | Gough et al. | |
| 5,843,016 A | 12/1998 | Lugnani et al. | |
| 5,871,483 A | 2/1999 | Jackson et al. | |

| | | | |
|---|---|---|---|
| 5,891,135 | A | 4/1999 | Jackson et al. |
| 5,989,284 | A | 11/1999 | Luafer |
| 6,009,877 | A | 1/2000 | Edwards |
| 6,016,437 | A * | 1/2000 | Tu et al. ............... 600/374 |
| 6,036,689 | A * | 3/2000 | Tu et al. ............... 606/41 |
| 6,048,329 | A * | 4/2000 | Thompson et al. ...... 604/95.04 |
| 6,056,744 | A * | 5/2000 | Edwards ............... 606/41 |
| 6,091,995 | A * | 7/2000 | Ingle et al. ............ 607/138 |
| 6,099,526 | A * | 8/2000 | Whayne et al. .......... 606/41 |
| 6,106,521 | A * | 8/2000 | Blewett et al. .......... 606/41 |
| 6,142,993 | A * | 11/2000 | Whayne et al. .......... 606/41 |
| 6,165,172 | A * | 12/2000 | Farley et al. ........... 606/33 |
| 6,168,594 | B1 | 1/2001 | LaFontaine et al. |
| 6,190,382 | B1 * | 2/2001 | Ormsby et al. .......... 606/33 |
| 6,200,333 | B1 | 3/2001 | Laufer |
| 6,283,989 | B1 | 9/2001 | Laufer |
| 6,440,128 | B1 | 8/2002 | Edwards et al. |

FOREIGN PATENT DOCUMENTS

| | | |
|---|---|---|
| GB | 2269538 | 2/1994 |
| WO | WO 92/10142 | 6/1992 |
| WO | WO 93/08755 | 5/1993 |
| WO | WO 94/10925 | 5/1994 |
| WO | WO 94/26178 | 11/1994 |
| WO | WO 95/08289 | 3/1995 |
| WO | WO 95/18575 | 7/1995 |
| WO | WO 95/19142 | 7/1995 |
| WO | WO 96/29946 | 10/1996 |
| WO | WO 97/32532 | 9/1997 |

OTHER PUBLICATIONS

Slepian, M.; "Polymeric Endoluminal Paving and Sealing"; 1990; from Textbook of Interventional Cardiology, WB Saunders Publishing, Philadelphia.

Tissue, B.; "Electromagnetic Spectrum"; Copyright 1996; retrieved online from http://www.chem.ufl.edu/~itl/3417_s98/spectroscopy/em-spec.htm, originally on website http://www.scimedia.com/checm-ed/light/edm-spec.htm, updated Nov. 3, 1996, 1 page.

Kaneko, et al., "Physiological Laryngeal Pacemaker", 1985, Trans Am Soc Artif Intern Organs, vol. XXXI, pp. 293-296.

Mugica, et al., "Direct Diaphragm Stimulation", Jan.-Feb. 1987, Part II, PACE, vol. 10, pp. 252-256.

Mugica, et al., "Preliminary Test of a Muscular Diaphragm Pacing System on Human Patients, Chapter 21", Neurostimulation: An Overview, 1985, pp. 263-279.

Nochomovitz, et al., "Electrical Activation of the Diaphragm", Jun. 1988, Clinics in Chest Medicine, vol. 9, No. 2, pp. 349-358.

Prior, et al., "Treatment of Menorrhagia by Radiofrequency Heating", 1991, Int. J. Hyperthermina, vol. 7, No. 2, pp. 213-220.

Rice, et al., "Functional Endoscopic Paranasal Sinus Surgery, The Technique of Messerklinger", Chapter 5, Endoscopic Paranasal Sinus Surgery, Raven Press, 1988, pp. 75-102.

Rice, et al., "Total Endoscopic Sphenoethmoidectomy, The Technique of Wigand", Chapter 6, Endoscopic Paranasal Sinus Surgery Raven Press, 1988, pp. 103-124.

* cited by examiner

TREATMENT OF TISSUE IN SPHINCTERS, SINUSES, AND ORIFICES

CROSS REFERENCE TO RELATED APPLICATIONS

This application is a continuation of U.S. patent application Ser. No. 09/356,110 filed Jul. 16, 1999, now U.S. Pat. No. 7,022,105, which is included herein by this reference thereto and which is a continuation-in-part of U.S. patent application Ser. No. 08/717,612 filed Sep. 20, 1996, now U.S. Pat. No. 6,077,257.

BACKGROUND OF THE INVENTION

1. Field of the Invention

This invention relates to treatment of tissue, particularly in the sphincters, esophagus, sinuses and other internal body orifices and structures. Such treatment can be performed using ablation, coating, expansion, plumping, shaping, shrinking, or related techniques.

2. Related Art

Human beings are subject to a number of disorders in the sphincters, sinuses, esophagus and other internal orifices. Disorders in the rectum and colon include hemorrhoids (external and internal), fecal incontinence, prolapsed rectal muscles, rectal muscle spasms, anal fissures, polyps, diverticulosus, diverticulitis, and pilonital cysts. Other internal disorders in nearby regions of the male body include prostate cancer, blockage of the urethra and incontinence. Other internal disorders in nearby regions of the female body include incontinence, vaginal bleeding, vaginal cysts, vaginal fibroids, prolapsed uterus, and related tumors or cancerous tissue. Disorders of the pharynx include tumors and polyps in the hypopharynx, oropharynx and nasopharynx. Disorders in adjacent structures include Barrett's esophagus, laryngeal tumors and laryngeal polyps.

Known methods for the treatment of these disorders include surgery, pharmaceutical remedies, chemotherapeutic regimens, radiation, photodynamic therapy and lifestyle modification. These methods only occasionally achieve the goal of successful treatment of disorders in orifices, sphincters, esophagus and sinuses. Moreover, these methods suffer from several drawbacks.

Drawbacks to surgical treatment include its highly invasive nature, associated risks, possible iatrogenic effects, and high cost. Drawbacks to pharmaceutical and chemotherapeutic treatments include their relative ineffectiveness (particularly in the oral cavity and adjacent respiratory structures) and associated side effects. Moreover, these approaches are contraindicated for many patients. Drawbacks to lifestyle modification include relatively poor patient compliance and relative ineffectiveness. Drawbacks to photodynamic therapy include its frequent unavailability and limited applicability. Drawbacks to radiation include side effects such as exhaustion, radiation burns, chronic dry mouth and permanent distortion of the taste buds. Accordingly, it would be advantageous to provide techniques for treatment of these disorders that are not subject to these known drawbacks.

The use of radio frequency (RF) to ablate tissue in the body (such as heart muscle) is known in the art of cardiac treatment. However, known systems using RF energy are sill subject to several drawbacks. One known problem is that it can be difficult to block the flow of bodily fluids and gases into an area of the body where tissue ablation is taking place. Bodily fluids can dissipate and detrimentally absorb the energy to be applied to the tissue to be ablated. Dissipation of bodily fluids detracts from the goal of successful tissue ablation and etching.

A second known problem in the art involves directing and positioning the electrodes in the body cavity or orifice. Difficulties in accurately positioning the electrodes in the target orifice detract from treatment. Frequently, unhealthy tissue can remain unablated while healthy tissue is removed. Difficulties in directing and positioning the electrodes are particularly problematic because one of the goals of treatment is to minimize collateral damage to healthy tissue and to completely ablate diseased tissue.

A third known problem in the art involves difficulty in the simultaneous use of complimentary technology. Known systems do not provide for optimal, simultaneous use of auxiliary tools for visualization, feedback technology and drug administration.

Accordingly, it would be advantageous to provide improved techniques for treatment of disorders in the esophagus, sphincters, sinuses and other internal body orifices. For example, it would be advantageous to provide devices bearing different arrays of curvilinear electrodes that can be retracted or extended into the target tissue that can also support apparatus for drug administration and tissue visualization. Such devices would allow medical personnel to (1) visualize the tissue to be ablated or etched, (2) seal off the area from fluids and gases that would disturb the area to be ablated (3) ablate all diseased tissue while sparing healthy tissue and (4) provide for the localized administration of drugs to numb the area and treat the disorder. These advantages are achieved in an embodiment of the invention in which medical personnel use a catheter bearing multiple controls for visualization and drug administration, balloon-like air sacs for sealing the area and multiple arrays of curvilinear electrodes that can be extended and retracted as needed.

SUMMARY OF THE INVENTION

The invention provides a method and system for treatment of body structures or tissue. The particular treatment can include one or more of, or some combination of ablation, coating, expansion, plumping, shaping, shrinking, or related techniques. The particular body structures or tissue can include one or more of, or some combination of regions, including a sphincter, sinus or orifice such as the rectum, colon, esophagus, vagina, penis, larynx or pharynx.

In one aspect of the invention, an environment proximate to or surrounding the targeted treatment region can be isolated or controlled by blocking the flow of gases or liquids using an inflatable balloon positioned immediately adjacent to the tissue that is to be ablated. The inflatable balloon can also serve to anchor the catheter in place and prevent the catheter from being expelled from the body. The inflatable balloon can also insure that locally administered drugs remain in the area where most needed.

In a second aspect of the invention, positive pressure is used to inflate the balloon. Inflation of the balloon triggers the extension of at least one curvilinear electrode into the targeted tissue. Negative pressure deflates the air sac and helps retract the curvilinear electrodes so as to allow the catheter to be removed from the body without damaging adjacent body structures. Alternately, the electrode(s) can be extended or retracted from the tissue, independently from the act of inflation or deflation of the balloon.

In a third aspect of the invention, the electrodes are coupled to sensors that measure properties of the target region, such as temperature and impedance. Measurement of these properties permits the use of feedback technique to control delivery of the RF energy and administration of fluids for cooling and hydrating the affected tissues. The electrodes can also be coupled to radio opaque markers to aid in fluoroscopic positioning.

In a fourth aspect of the invention, the catheter includes an optical path that can be coupled to external viewing apparatus. In this way, the position of the electrodes in the body can be determined using fiber optic techniques. The external viewing apparatus can also be coupled to an ultrasound probe included in the catheter.

DETAILED DESCRIPTION OF THE INVENTION

System Elements

Figure 1:
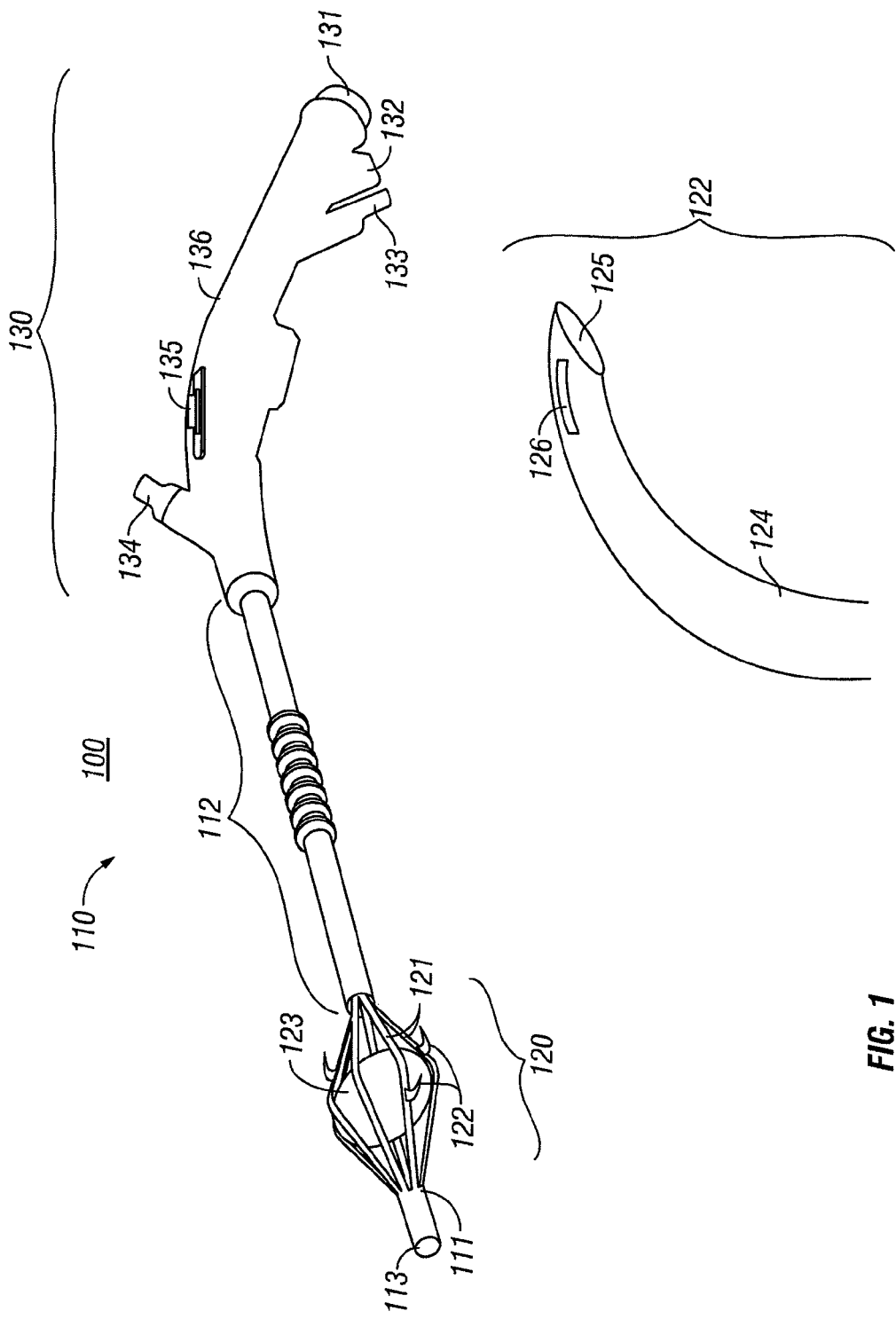
FIG. 1 is a block diagram of a system for ablating tissue using a catheter and electrode assembly according to the invention.

FIG. 1 is a block diagram of a system for ablating tissue associated with the rectal sphincter, esophagus, urethra and other internal body structures using a catheter and electrode assembly.

A catheter and electrode assembly 100 for treating tissue includes a catheter 110, an expandable cage structure 120 and a control and delivery linkage 130.

The catheter 110 includes a distal segment 111 and a proximal segment 112. The distal segment includes a tapered tip 113 for easy insertion into an orifice. The tapered tip 113 may be either flexible or rigid depending upon the orifice into which the catheter 110 is to be inserted. The overall length of the shaft of the catheter 110 (including the expandable cage structure 120) from the tapered tip 113 to the junction where the catheter 110 is coupled to the control and delivery linkage 120 is about 65 centimeters. The diameter of the catheter 110 is about 0.4 centimeters. In an alternative embodiment, the length and diameter of the shaft of the catheter 110 may vary substantially depending upon the application.

The catheter 110 includes an expandable cage structure 120. The cage structure 120 includes a set of struts 121, a set of curvilinear electrodes 122 and an inflatable balloon 123.

One end of each one of the struts 121 is coupled to the distal segment 111 of the catheter 110; the opposite end of each one of the set of struts 121 is coupled to the proximal segment 112 of the catheter. Taken together, the distal segment 111, the cage structure 120 and the proximal segment 112 are linearly contiguous and form one continuous unit. The inflatable balloon 123 is surrounded by the set of struts 121.

The set of curvilinear electrodes 122 is embedded in the set of struts 121. The electrodes 123 each include a metallic tube 124 defining a hollow lumen 125, shaped similarly to a curvilinear needle and a sensor 126. In addition to ablating tissue by delivering RF energy, the electrodes 113 are disposed to deliver at least one flowable substance to the area of the body where ablation is to take place. In a preferred embodiment, the flowable substance includes saline with a concentration of less than about 10% NaCl, which aids in hydration of body structures. However, in alternative embodiments, the deliverable flowable liquids includes other substances, including anesthetic drugs, anti-inflammatory agents, chemotherapeutic agents, systemic or topical antibodies, collagen and radioactive substances, such as labeled tracers.

Exact positioning of the electrodes 122 is achieved by inflating the balloon 123. Inflation of the balloon 123 causes expansion of the expandable cage structure 120, allowing one or more of the set of electrodes 122 to be extended directly into the targeted tissue.

The assembly 110 is operated by manipulating the control and delivery linkage 130. The control and delivery linkage 130 includes a port 131, two female couplings 132 and 133, a mechanical switch 135 and a hand set 136.

The port 131 can be coupled to both a RF source and a visualization apparatus, such as fiber optic devices or fluoroscopy equipment, to allow internal viewing of the orifice. The two female couplings 132 and 133 can be coupled to a syringe or other device to which positive pressure can be applied to inflate the balloon 123. In a preferred embodiment, one or more of the female couplings 132, 133 and 134 can also be coupled to drug administration apparatus. Manipulation of the mechanical switch 135 causes the extension of the electrodes 122. The female couplings 132, 133 and 134, mechanical switch 135 and port 131 are all located immediately adjacent to the hand set 136 to allow easy operation.

First Method of Operation

Figure 2:
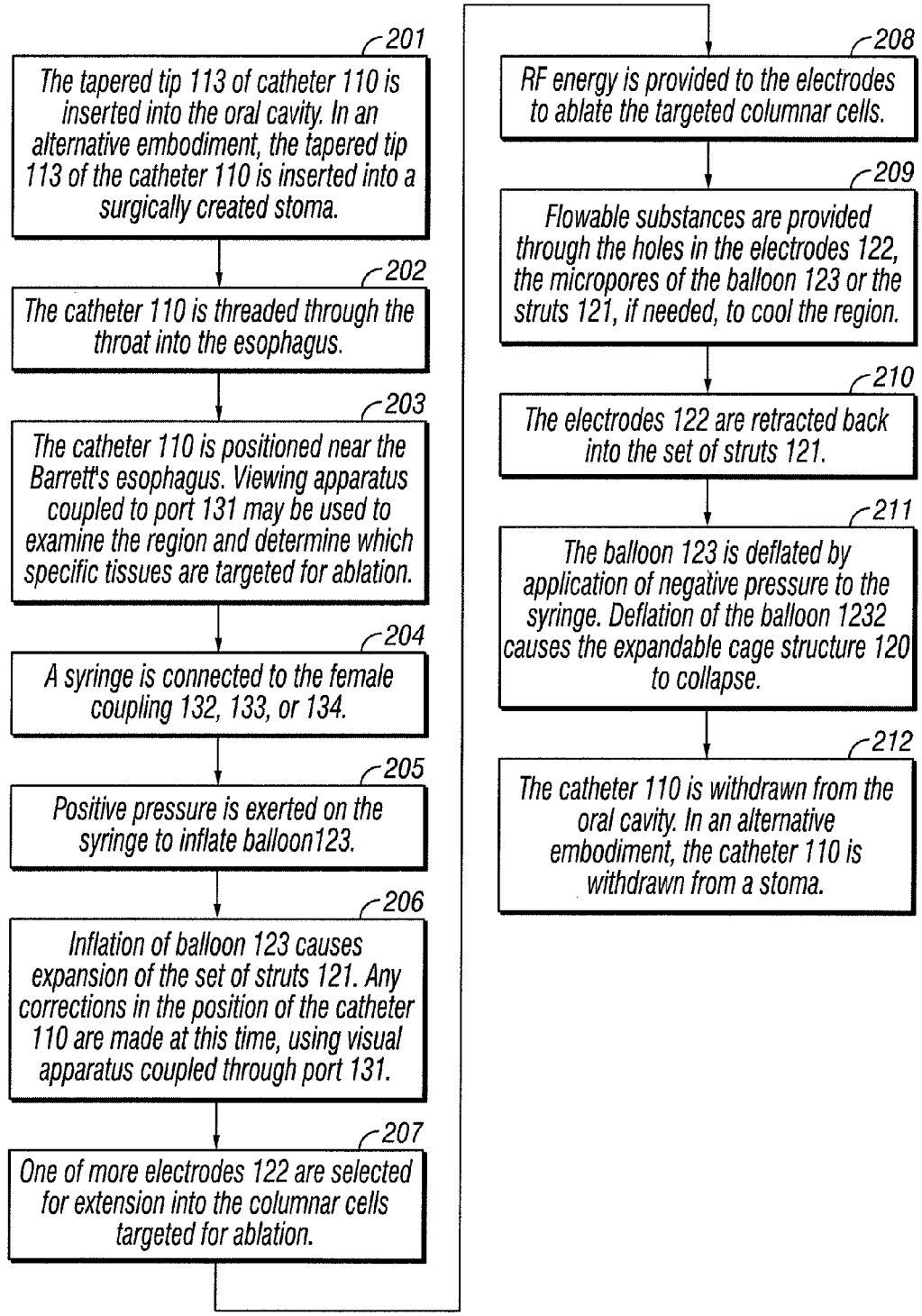
FIG. 2 is a process flow diagram of a method for treatment for Barrett's esophagus according to the invention.

FIG. 2 is a process flow diagram of a method for treatment of Barrett's esophagus.

A method 200 is performed using a catheter and electrode assembly 100.

In a step 201, the tapered tip 113 of the catheter 110 is inserted into the oral cavity. Due to the potential for inducing pain or a gag reflex, the oral cavity is preferably pretreated with lidocaine spray or other topical anesthetic before insertion; depending upon the circumstances, a muscle relaxant may be indicated. In an alternative embodiment, the tapered tip 113 of the catheter 110 is inserted into a surgically created stoma.

The preferred size of the catheter 110 will be responsive to the orifice through which the catheter is inserted. The choice of pharmaceutical agents to be infused prior to or during treatment will be responsive to judgments by medical personnel, and may include lubricants, anesthetics, antispasmodics, anti-inflammatories, antibiotics or other agents.

In a step 202, the catheter 110 is threaded through the throat into the esophagus. Precautions are preferably taken to ensure that the catheter 110 is not threaded through the trachea into the lungs.

In a step 203, the catheter 110 is positioned near the Barrett's esophagus. In the preferred embodiment, viewing apparatus coupled to the port 131 may be used to examine the region and determine which specific tissues are targeted for ablation. Healthy tissue composed of white squamous cells is distinguished from unhealthy pink columnar cells indicative of Barrett's esophagus.

In a step 204, a syringe is connected to the female coupling 132, 133 or 134.

In a step 205, the syringe is used to exert positive pressure and inflate the balloon 123 with a flowable substance, such as air or liquid. Inflation of the balloon 123 serves several purposes. In addition to positioning the electrode 122, the balloon 123 also helps anchor the catheter 110 and prevents gas or liquids arising in the stomach from contaminating the region.

In a step 206, inflating of the balloon 123 causes expansion of the set of struts 121. Any corrections in the positioning of the catheter 110 are made at this time, using the visual apparatus coupled through the port 131.

In a step 207, one or more electrodes 122 are selected for extension into the columnar cells targeted for treatment. The particular treatment can include one or more of, or some combination of, ablation, coating, expansion, plumping, shaping, shrinking, or related techniques. The mechanical switch 134 is used to extend at least one electrode 122 into the targeted columnar cells.

In a step 208, RF energy is provided to the electrodes so as to ablate the targeted columnar cells. In a preferred embodiment, the RF energy has a frequency between 435 and 485 kilohertz. The tissue immediately near the electrodes receives the RF energy. The strength and duration of time the energy is applied are responsive to judgments by medical personnel. In alternative embodiments, the electrodes may deliver other forms of energy, such as heat, microwaves, infrared or visible laser energy. In other alternative embodiments, the electrodes are controlled by a feedback technique using at least one sensor 126, such as an impedance or temperature sensor.

To perform ablation, the tissue is heated for a short period of time until ablation occurs. Application of RF energy causes cell death by dehydration or denaturation of cellular proteins.

To perform expansion, plumping, or shaping, the tissue is suffused with a flowable substance, such as a gas or liquid, a collagen, or another substance that can be absorbed by the body structure or tissue. The flowable substance can be exuded from the catheter, either using a separate flow line, or using the electrodes themselves. In a preferred embodiment, the tissue is heated for a short time, and thereafter cooled, so as to cause the flowable substance to crosslink or otherwise transform into a bulking, plumping, or shaping agent.

To perform coating, the flowable substance can be exuded so as to adhere to (or be adsorbed by) an epithelial layer of cells. In a preferred embodiment, the tissue is heated for a short time, and thereafter cooled, so as to cause the flowable substance to crosslink or otherwise transform into a solid mass coating or covering the epithelial layer.

To perform shrinking, the tissue is suffused with the flowable substance, with the flowable substance being selected so as to act as a receiving antenna or dielectric for the RF energy. RF energy is applied, which is differentially absorbed by the flowable substance; this causes the flowable substance to heat and to shrink the tissue is suffused, either by cell death, dehydration, or denaturation of cellular proteins.

In a step 209, flowable substances are provided through the holes in the electrodes 122, the micropores of the balloon 123 or from the struts 121, if needed to immediately cool down the region and prevent collateral thermal damage. The nature, temperature and amount of the flowable substance are responsive to judgments by medical personnel.

In a step 210, the electrodes 122 are retracted back into the set of struts 121.

In a step 211, the balloon is deflated by negative pressure on the syringe. Deflation of the balloon 123 causes the expandable cage structure 120 to collapse.

In a step 212, the catheter 110 is withdrawn from the oral cavity. In an alternative embodiment, the catheter 110 is withdrawn from a stoma.

Second Method of Operation

Figure 3:
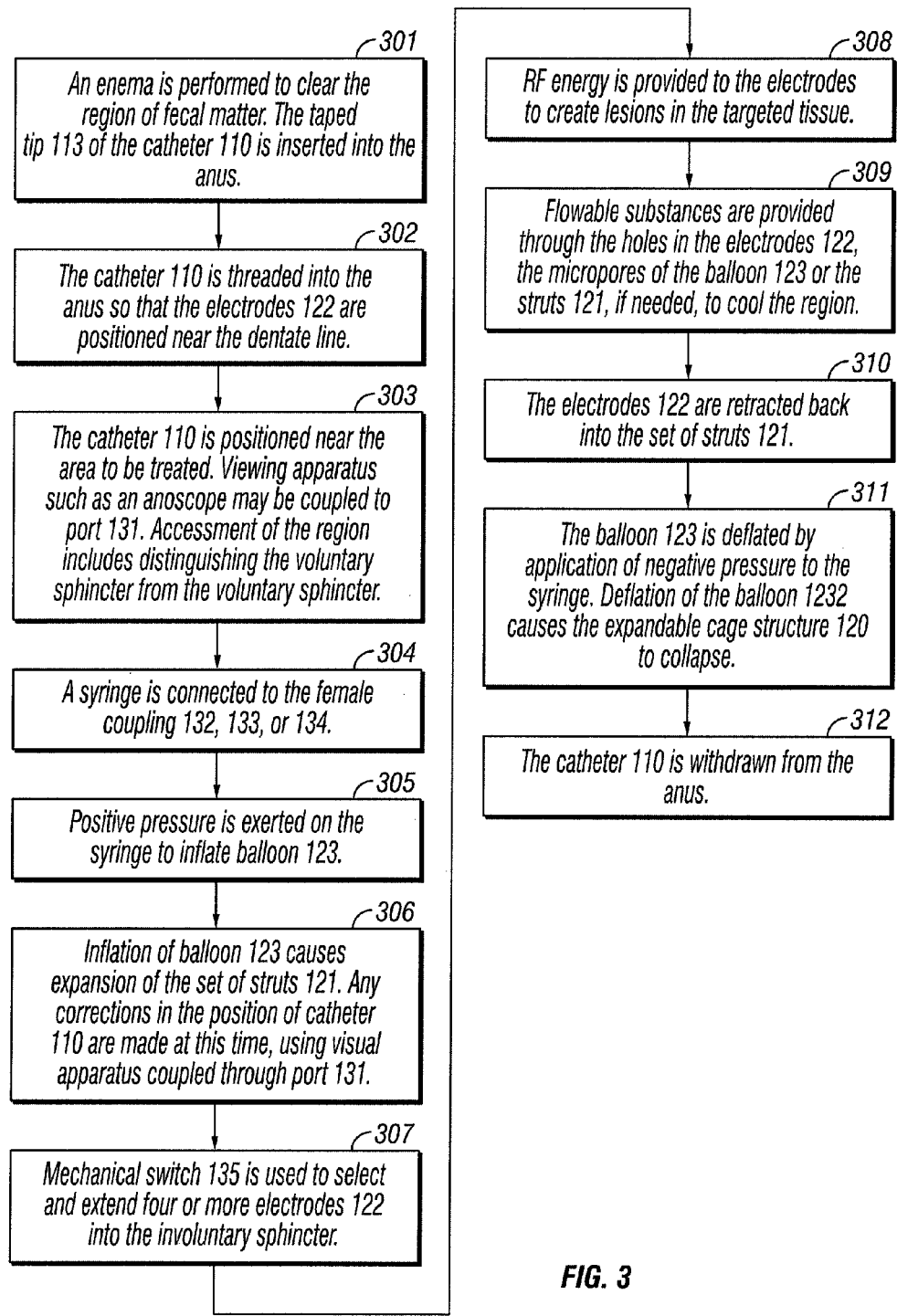
FIG. 3 is a process flow diagram of a method for treatment of fecal incontinence according to the invention.

FIG. 3 is a process flow diagram of a method for treatment of fecal incontinence.

A method 300 is performed using a catheter and electrode assembly 100. This method requires the use of four to eight electrodes and a blunt tapered tip 113.

In a step 301, an enema is performed to clear the region of fecal matter. The rectum and surrounding area are washed with a cleansing agent, such as benzalonium chloride. A topical anesthetic may be applied to prevent pain associated with insertion; depending upon the circumstances, a muscle relaxant may be indicated. The tapered tip 113 of the catheter 110 is inserted into the anus.

The preferred size of the catheter 110 will be responsive to the orifice through which the catheter is inserted. The choice of pharmaceutical agents to be infused prior to or during treatment will be responsive to judgments by medical personnel, and may include lubricants, anesthetics, antispasmodics, anti-inflammatories, antibiotics or other agents.

In a step 302, the catheter 110 is threaded into the anus so that the electrodes 122 are positioned neat the dentate line.

In a step 303, the catheter 110 is positioned neat the area to be treated. In the preferred embodiment, viewing apparatus, such as an anoscope coupled to port 131 may be used to examine the region and determine which specific tissues are targeted for ablation. In an alternative embodiment, the area can be accessed using a colorectal ultrasound probe. It is important to distinguish between the voluntary and involuntary sphincter because fecal incontinence is frequently causes by defects in the involuntary sphincter. One of the goals of treatment is to avoid exacerbating the incontinence problem by injuring the voluntary sphincter.

In a step 304, a syringe is connected to the female coupling 132, 133 or 134.

In a step 305, the syringe is used to exert positive pressure and inflate the balloon 123 with air or with a liquid. Inflation of the balloon 123 serves several purposes. In addition to positioning the electrode 122, the balloon 123 also helps anchor the catheter 110 and prevents gas, liquid or fecal matter from contaminating the region. If necessary, a second balloon can be used to anchor the catheter distally.

In a step 306, inflation of the balloon 123 causes expansion of the set of struts 121. Any corrections in the positioning of the catheter 110 are made at this time, using the visual apparatus coupled through the port 131.

In a step 307, four or more electrodes 122 are selected for extension into the involuntary sphincter. The mechanical switch 135 is used to extent the electrodes 122 into the involuntary sphincter. Thermal injury to sensitive female structures is avoided by selecting electrodes 122 in area other than the anterior portion of the anus. In both sexes, treatment is directed to the area one to two centimeter above and up to one centimeter below the dentate line. Highly innervated regions of tissue are avoided so as to minimize pain.

In a step 308, RF energy is provided to the electrodes until thermal lesions are created in the targeted area(s). In a preferred embodiment, the RF energy has a frequency between 435 kilohertz and 485 kilohertz. The RF energy is received by the tissue immediately near the electrodes. The tissue is heated for a short period of time until ablation occurs. Application of RF energy causes cell death by dehydration and denaturization of cellular proteins. The strength and duration of time the energy is applied are responsive to judgments by medical personnel. In alternative embodiments, the electrodes may deliver other forms of energy, such as heat, microwaves, infrared or visible laser energy. In other alternative embodiments, the electrodes are controlled by a feedback technique using at least one sensor 126, such as an impedance or temperature sensor.

In a step 309, flowable substance are provided through holes in the electrodes 122, the struts 121 or the micropores of the balloon 123 if needed to immediately cool down the region and prevent collateral thermal damage. The nature, temperature and amount of the flowable substance are responsive to judgments by medical personnel.

In a step 310, the electrodes 122 are retracted back into the set of struts 121.

In a step 311, the balloon 123 is deflated by negative pressure on the syringe. Deflation of the balloon 123 causes the expandable cage structure 120 to collapse.

In a step 312, the catheter is withdrawn from the anus.

Third Method of Operation

Figure 4:
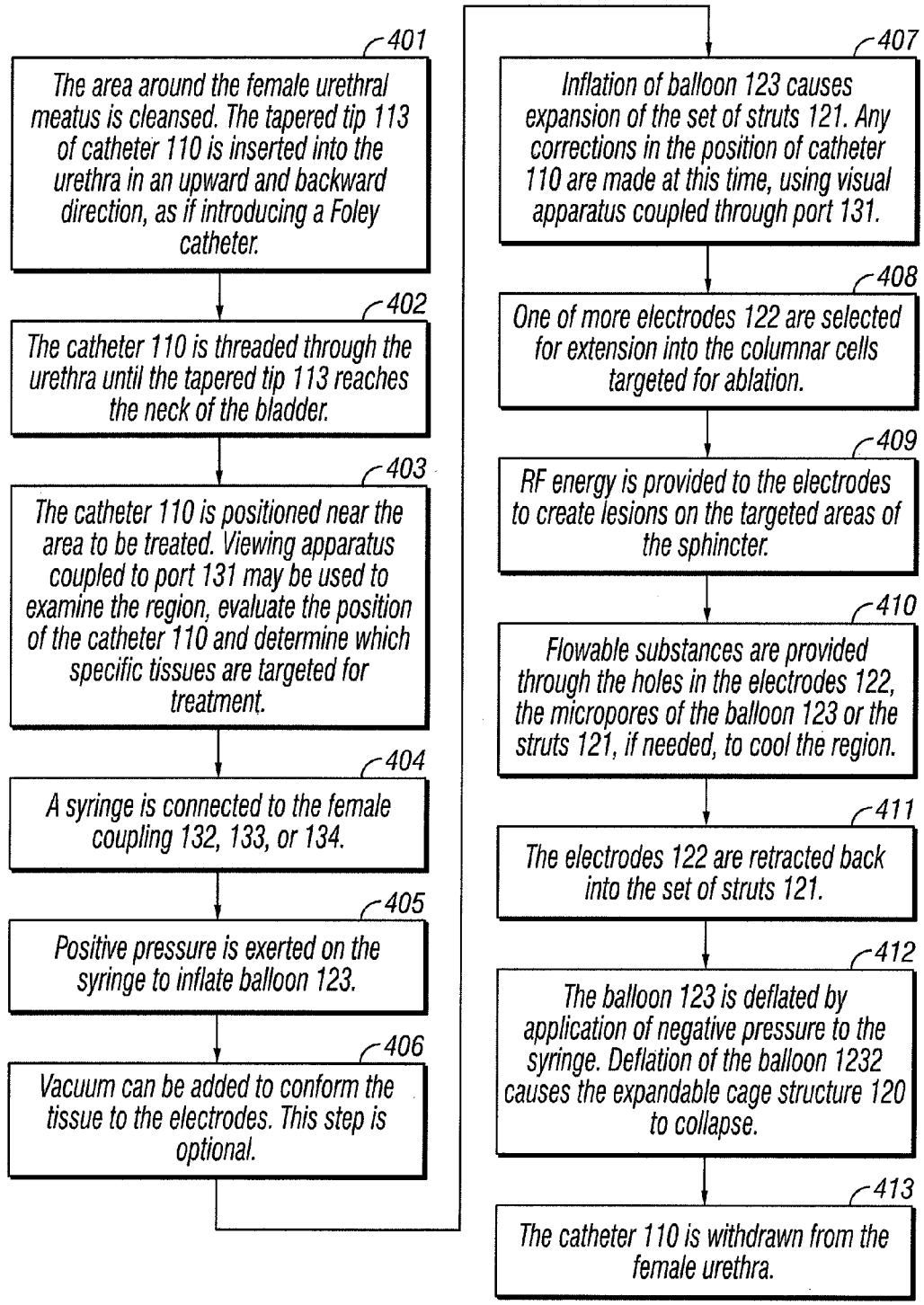
FIG. 4 is a process flow diagram of a method for treatment of female urinary incontinence according to the invention.

FIG. 4 is a process flow diagram of a method for treatment for female urinary incontinence.

A method 400 is performed using a catheter and electrode assembly 100.

In a step 401, the area around the urethral meatus is cleansed. The tapered tip of the catheter 110 is well lubricated and introduced into the urethral meatus in an upward and backward direction, in much the same way one would introduce a Foley catheter. Due to the potential for inducing pain, the outer opening of the urethra may be pretreated with a topical anesthetic before treatment. The choice of pharmaceutical agents to be infuse prior to or during treatment will be responsive to judgments by medical personnel and may include lubricants, anesthetics, antispasmodics, anti-inflammatories, antibiotics or other agents.

In a step 402, the catheter 110 is threaded through the urethra until the tapered tip 113 reaches the neck of the bladder using strict aseptic technique.

In a step 403, viewing apparatus coupled to part 131 may be used to examine the region and determine which area of the urethral sphincter is targeted for treatment. Ultrasound or fluoroscopy can also be used for positioning.

In a step 404, a syringe is connected to the female coupling 132, 133 or 134 included in the control and delivery linkage 130.

In a step 405, the syringe is used to exert positive pressure and inflate the balloon 123 with air or liquid. Inflation of the balloon 123 serves several purposes. In addition to positioning the electrode 122, the balloon 123 also helps anchor the catheter 110. In an alternative embodiment, a second balloon 123 is used to help position the bladder neck and seal it off.

In a step 406, vacuum can be added to conform the tissue to the electrodes. This step is particularly advantageous for patients whose pelvic floor muscles are in poor condition. This step is optional.

In a step 407, inflation of the balloon 123 causes expansion of the expandable cage structure 120. Expansion of the cage structure brings the electrodes 122 into immediate contact with the urinary sphincter. Any correction to the position of the catheter 110 is made at this time, using the visual apparatus coupled through part 131.

In a step 408, one or more electrodes 122 are selected for extension into tissue targeted for ablation. The mechanical switch 135 is used to extend at least one electrode 122 into the targeted tissue.

In a step 409, RF energy is provided to the electrodes to create lesions on the targeted tissue. In a preferred embodiment, the RF energy has a frequency between 435 and 485 kilohertz. The RF energy is received by the tissue immediately near the electrodes for a period of time less than ten minutes. The device can be repositioned by rotation or translation so the RF energy is delivered to multiple sites to create a pattern of lesions over several centimeters of tissue. The duration of time and frequency of energy are responsive to judgments of medical personnel. Creation of these lesions has the effect of causing the involuntary sphincter to shrink so that urine does not seep through. In alternative embodiments, muscle contraction can be achieved by application of chemical stimulation.

In a step 410, flowable substances are provided through holes in the electrodes 122, the struts 121 and/or micropores of the balloon 123, if needed, to lower the temperature of the region and prevent collateral thermal damage. The nature, temperature and amount of flowable substance are responsive to judgments by medical personnel.

In a step 411, the electrodes 122 are retracted back into the set of struts 121.

In a step 412, the balloon 123 is deflated by application of negative pressure on the syringe. Deflation of the balloon 123 causes collapse of the expandable cage structure 120.

In a step 413, the catheter 110 is withdrawn from the urethra.

Fourth Method of Operation

Figure 5:
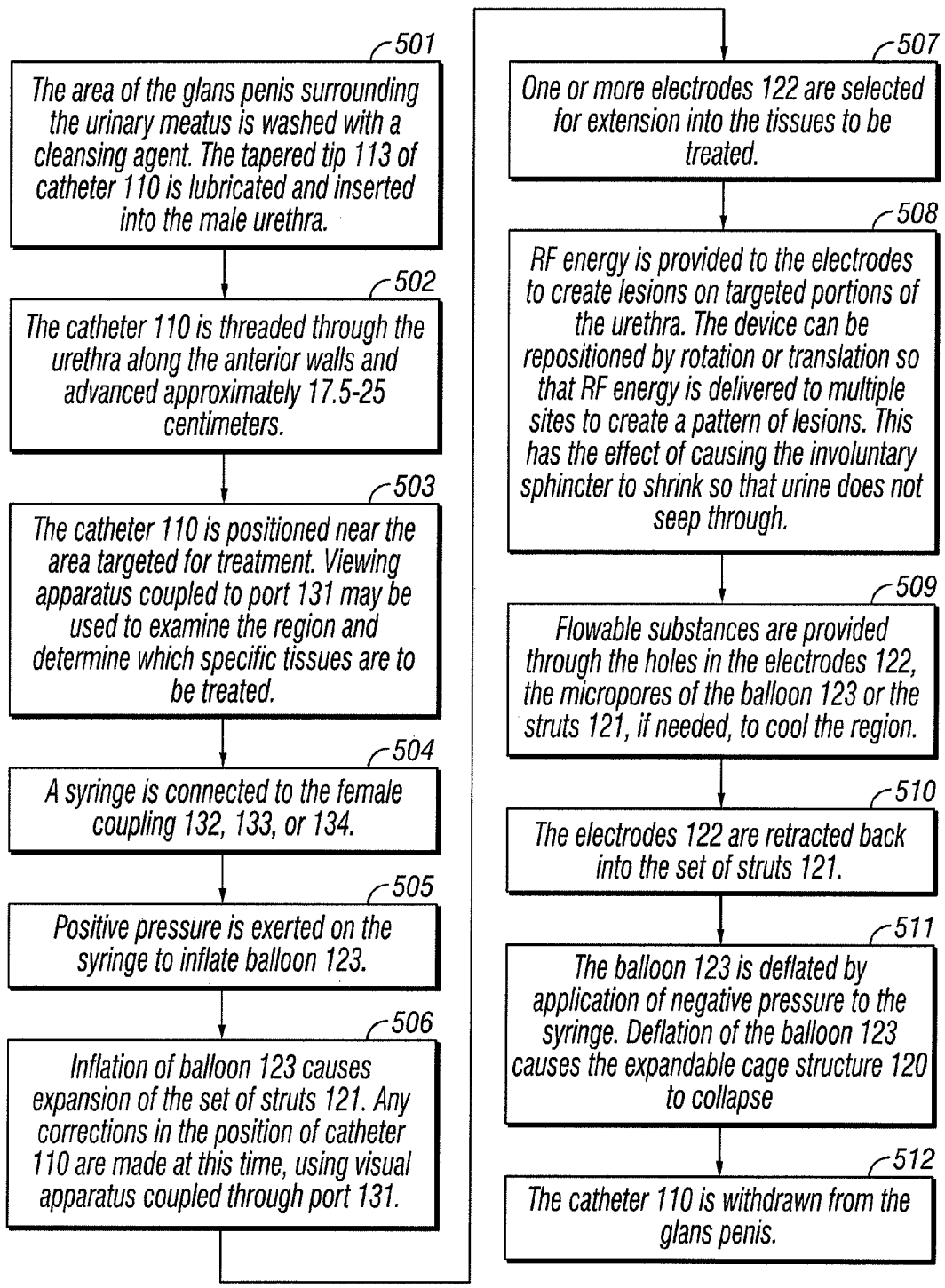
FIG. 5 is a process flow diagram of a method for treatment of male urinary incontinence according to the invention.

FIG. 5 is a process flow diagram of a method for treatment of male urinary incontinence.

A method 500 is performed using a catheter and electrode assembly 100.

In a step 501, the tapered tip 113 of the catheter 110 is well lubricated. The area of the glans penis around the urinary meatus is washed with a cleansing agent, such as benzalonium chloride. Due to the potential for inducing pain, the area surrounding the urinary means may be pretreated with a topical anesthetic before insertion; depending upon the circumstances, a muscle relaxant may be indicated.

The preferred size of the catheter 110 will be responsive to the orifice through which the catheter is inserted. The choice of pharmaceutical agents to be infused prior to or during treatment will be responsive to judgments by medical personnel, and may include lubricants, anesthetics, antispasmodics, anti-inflammatories, antibiotics or other agents.

In a step 502, the catheter 110 is introduced into the urethra along the anterior wall. The catheter is advanced 17.5-25 centimeters. Since the length from the bladder to the end of the glans penis varies, the distance that the catheter is advanced in responsive to the judgment of medical personnel.

In a step 503, the catheter 110 is positioned near the target area for treatment. In the preferred embodiment, viewing apparatus coupled to the port 131 may be used to examine the region and determine which specific tissues are targeted for treatment.

In a step 504, a syringe is connected to the female coupling 132, 133 or 134.

In a step 505, the syringe is used to exert positive pressure and inflate the balloon 123 with air or liquid. Inflation of the balloon 123 serves several purposes. In addition to positioning the electrode 122, the balloon 123 also helps anchor the catheter 110. If necessary, a second balloon 123, located distally, can also be inflated to anchor the balloon 123 in the bladder.

In a step 506, inflation of the balloon 123 causes expansion of the set of struts 121. Any corrections in the positioning of the catheter 110 are made at this time, using the visual apparatus coupled through port 131.

In a step 507, one or more electrodes 122 are selected for extension. The mechanical switch 135 is used to extend at least one electrode into the targeted tissue.

In a step 508, RF energy is provided to the electrodes so as to create lesions upon targeted regions of the urethra and bladder. In a preferred embodiment, the RF energy has a frequency between 435 and 485 kilohertz. The RF energy is received by the tissue immediately near the electrodes. The device can be repositioned by rotation or translation so that RF energy is delivered to multiple sites to create a pattern of lesions over several centimeters of tissue. Creation of these lesions has the effect of causing the involuntary sphincter to shrink so that urine does not seep through. In alternative embodiments, muscle contraction (and the consequence shrinkage of the involuntary sphincter) can be achieved by application of chemical stimulation. In other alternative embodiments, the electrodes are controlled by a feedback technique using at least one sensor 126, such as an impedance or temperature sensor.

In a step 509, flowable substances are provided through the holes in the electrodes 122, the struts 121 and/or the micropores in the balloon 123 if needed to immediately cool down the region and prevent collateral thermal damage. The nature, temperature and amount of the flowable substance are responsive to judgments by medical personnel.

In a step 510, the electrodes 122 are retracted back into the set of struts 121.

In a step 511, the balloon 123 is deflated by negative pressure on the syringe. Deflation of the balloon 123 causes the expandable cage structure 120 to collapse.

In a step 512, the catheter 110 is withdrawn from the glans penis.

Fifth Method of Operation

Figure 6:
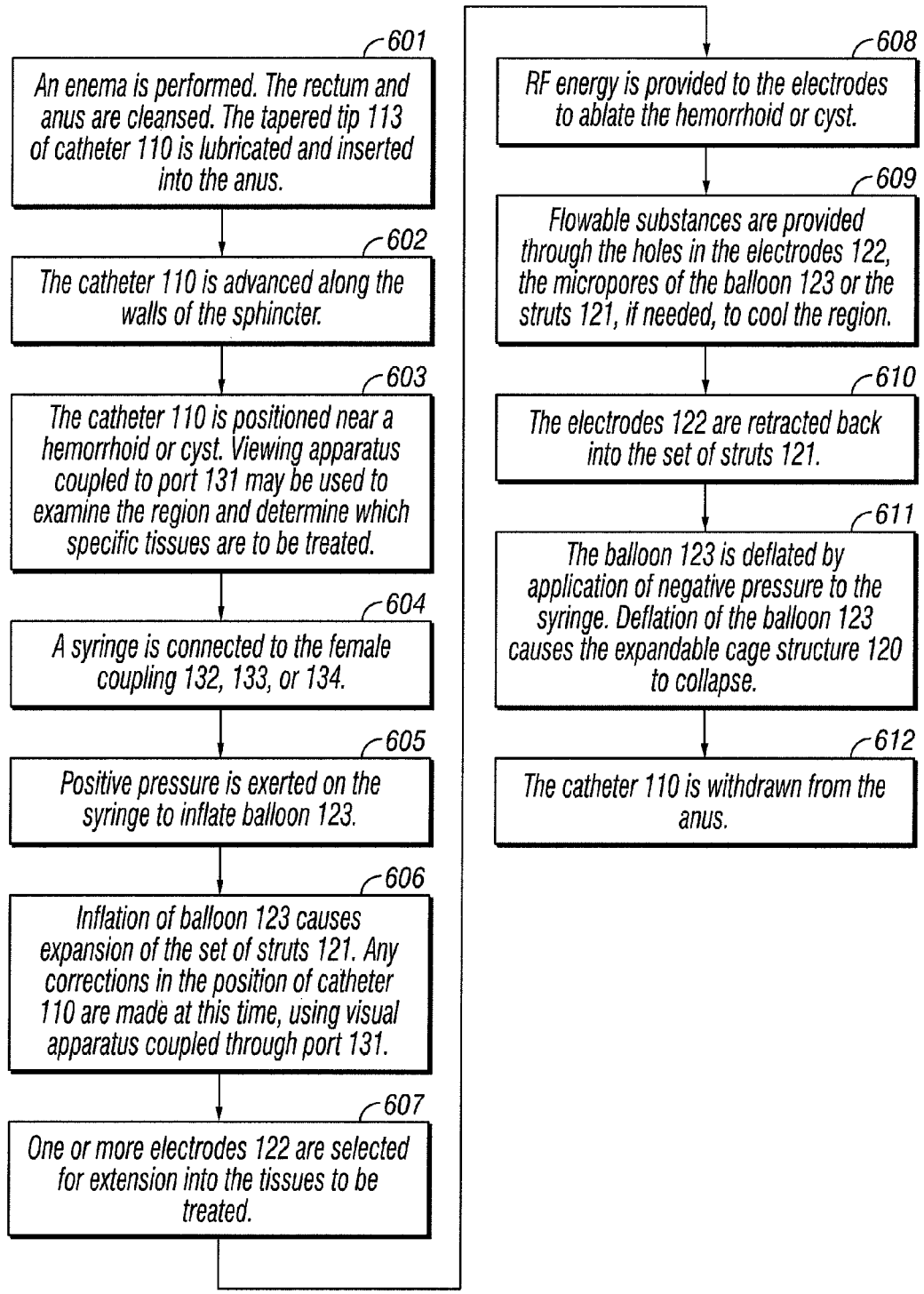
FIG. 6 is a process flow diagram of a method for treatment of a hemorrhoid or pilonital cyst according to the invention.

FIG. 6 is a process flow diagram of a method for treatment of a hemorrhoid.

A method 600 is performed using a catheter and electrode assembly 100.

In a step 601, the tapered tip 113 of the catheter 110 is well lubricated. An enema is performed to clear the area of fecal matter. The rectum and surrounding area are washed with a cleansing agent such as benzalonium chloride. Due to the potential for inducing pain, the area surrounding the rectum may be presented with a topical anesthetic before insertion; depending upon the circumstances, a muscle relaxant may be indicated.

The preferred size of the catheter 110 will be responsive to the orifice through which the catheter is inserted. The choice of pharmaceutical agents to be infused prior to or during treatment will be responsive to judgments by medical personnel, and may include lubricants, anesthetics, antispasmodics, anti-inflammatories, antibiotics or other agents.

In a step 602, the catheter 110 is introduced into the anus and advanced along the walls of the sphincter. Since hemorrhoids and pilonital cysts may occur anywhere along this passage, the distance that the catheter is introduced is responsive to the judgment of medical personnel.

In a step 603, the catheter is positioned near the internal hemorrhoid, external hemorrhoid or cyst that is targeted for ablation. In the preferred embodiment, viewing apparatus coupled to the port 131 may be used to examine the region and determine which specific tissues are targeted for ablation. Ultrasound or fluoroscopy may also be employed to help position the catheter 110.

In a step 604, a syringe is connected to the female coupling 132, 133 or 134.

In a step 605, the syringe is used to exert positive pressure and inflate the balloon 123 with air or with a liquid. Inflation of the balloon 123 serves several purposes. In addition to positioning the electrode 122, the balloon 123 also helps anchor the catheter 110, seal off the region and prevent contamination with fecal matter.

In a step 606, inflation of the balloon 123 causes expansion of the set of struts 121. Any corrections in the positioning of the catheter 110 are made at this time, using the visual apparatus coupled through port 131.

In a step 607, one or more electrodes 122 are selected for extension. The mechanical switch 135 is used to extend at least one electrode 122 into the targeted tissue.

In a step 608, RF energy is provided to the electrodes so as to ablate the hemorrhoid or cyst. In a preferred embodiment, the RF energy has a frequency between 435 and 485 kilohertz. The RF energy is received by the tissue immediately near the electrodes. The tissue is heated for a short period of time until ablation occurs. In an alternative embodiment, the electrodes are controlled by a feedback technique using at least one sensor 126, such as an impedance or temperature sensor.

In a step 609, flowable substances are provided through the holes in the electrodes 122, the struts 121 and/or the micropores of balloon 123 if needed to immediately cool down the region and prevent collateral thermal damage. The nature, temperature and amount of the flowable substance are responsive to judgments by medical personnel.

In a step 610, the electrodes 122 are retracted back into the set of struts 121.

In a step 611 the balloon 123 is deflated by negative pressure on the syringe. Deflation of the balloon 123 causes the expandable cage structure 120 to collapse.

Steps 605 through 611 are repeated as necessary until all hemorrhoids or cysts are removed.

In a step 612, the catheter 110 is withdrawn from the anus.

Sixth Method of Operation

Figure 7:
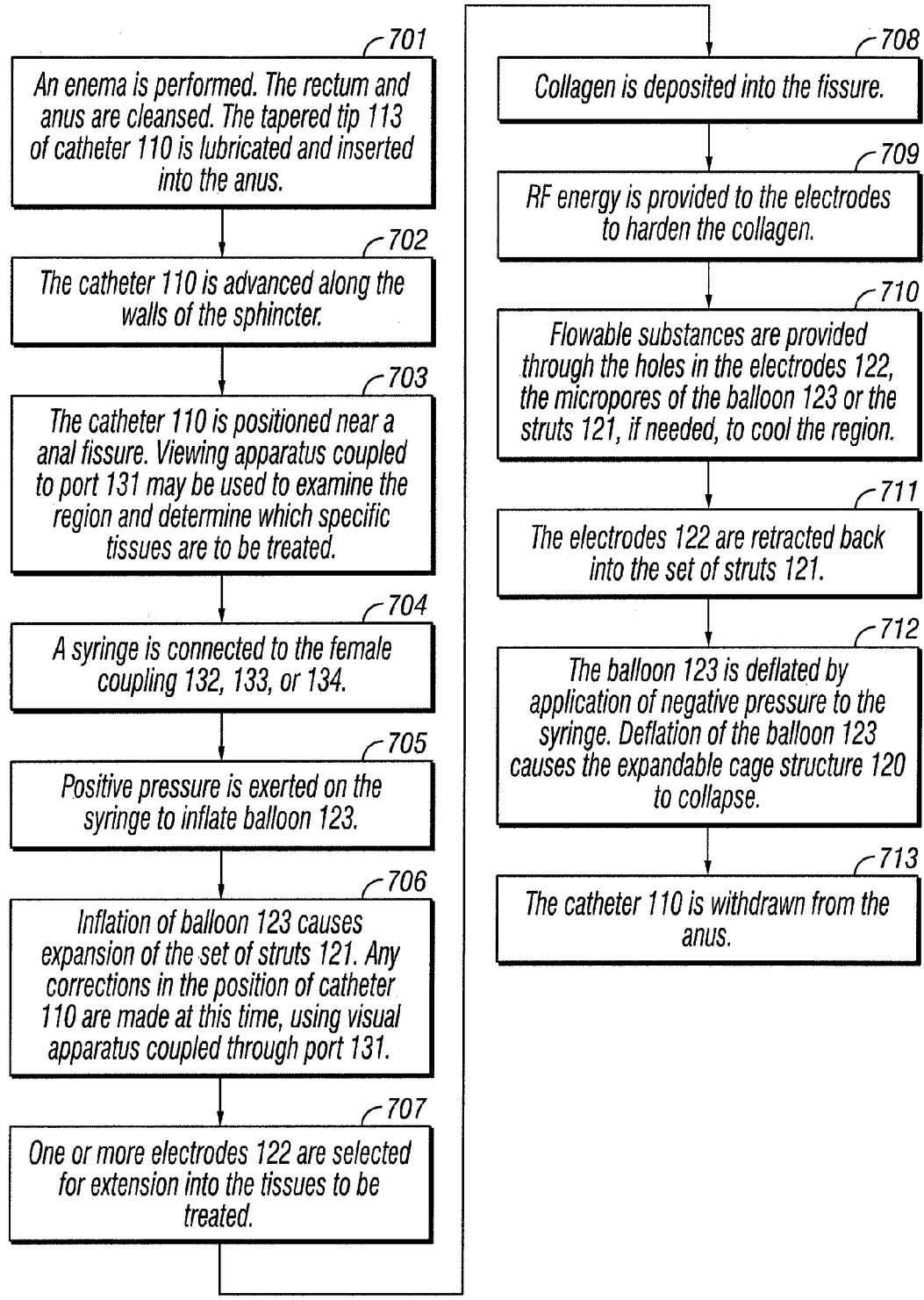
FIG. 7 is a process flow diagram of a method for treatment of an anal fissure according to the invention.
Figure 8:
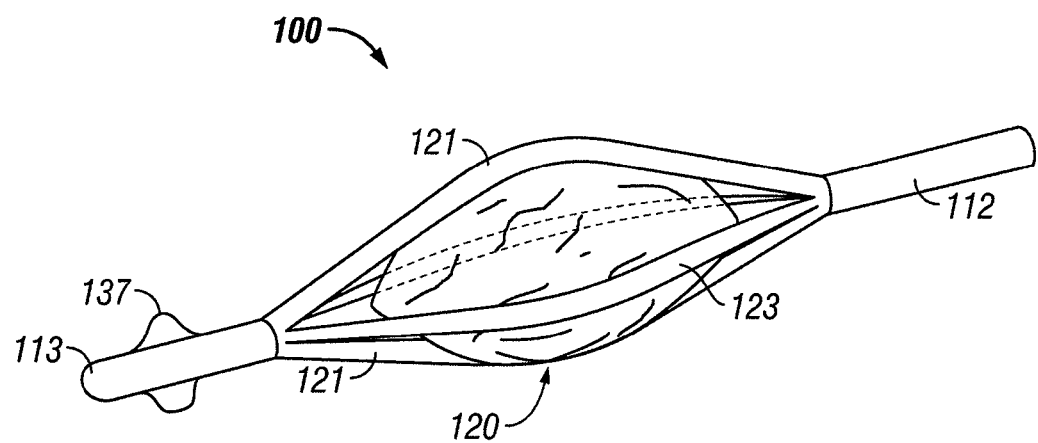
FIG. 8 shows an alternate embodiment of the apparatus of FIG. 1 according to the invention.
Figure 9:
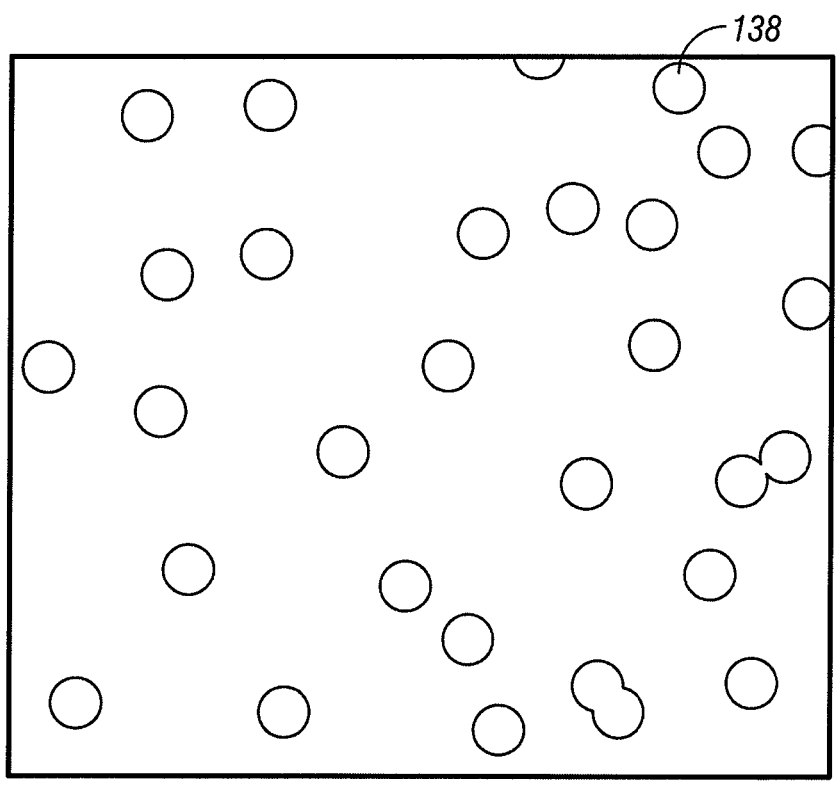
FIG. 9 shows a balloon having micropores according to the invention.

FIG. 7 is a process flow diagram of a method for treatment of an anal fissure.

A method 700 is performed using a catheter and electrode assembly 100.

In a step 701, the tapered tip 113 of the catheter 110 is well lubricated. An enema is performed to clear the region of fecal matter. The anus and rectal area are washed with a cleansing agent such as benzalonium chloride. Due to the potential for inducing pain, the area surrounding the anus may be pre-treated with a topical anesthetic before insertion; depending upon the circumstances, a muscle relaxant may be indicated.

The preferred size of the catheter 110 will be responsive to the orifice through which the catheter is inserted. The choice of pharmaceutical agents to be infused prior to or during treatment will be responsive to judgments by medical personnel, and may include lubricant, anesthetics, antispasmodics, anti-inflammatories, antibiotics or other agents.

In a step 702, the catheter 110 is introduced into the anus and advanced along the walls of the sphincter. The distance that the catheter 110 is introduced is responsive to the judgment of medical personnel.

In a step 703, the catheter 110 is positioned near an anal fissure. In the preferred embodiment, viewing apparatus coupled to the port 131 may be used to examine the region and determine which specific tissues are targeted for ablation and where collagen should be deposited. Ultrasound or fluoroscopic imaging can also be used to position the catheter 110.

In a step 704, a syringe is connected to the female coupling 132, 133 or 134.

In a step 705, the syringe is used to exert positive pressure and inflate the balloon 123 with air or with a liquid. Inflation of the balloon 123 serves several purposes. In addition to positioning the electrode 122, the balloon 123 also helps anchor the catheter 110. In an alternative embodiment, a second balloon 123 can be inflated, if necessary to help anchor the catheter 110.

In a step 706, inflation of the balloon 123 causes expansion of the set of struts 121. Any corrections in the position of the catheter 110 are made at this time, using the visual apparatus coupled through port 131.

In a step 707, one or more electrodes 122 are selected for extension. The mechanical switch 135 is used to extend at least one electrode 122 into the targeted tissue.

In a step 708, collagen is deposited into the fissure.

In a step 709, RF energy is provided to the electrodes so as to harden the collagen for filling the fissure. In a preferred embodiment, the RF energy has a frequency between 435 kilohertz and 485 kilohertz. The RF energy is received by the tissue immediately near the electrodes. The tissue is heated for a short period of time until the collagen is sufficiently hardened. In an alternative embodiment, the electrodes are controlled by a feedback technique using at least one sensor 126, such as an impedance or temperature sensor.

In a step 710, other flowable substances are provided through the holes in the electrodes 122, the struts 121 and/or the micropores of the balloon 123, if needed to immediately cool down the region and prevent collateral damage. The nature, temperature and amount of the flowable substance are responsive to judgments by medical personnel.

In a step 711, the electrodes 122 are retracted back into the set of struts 121.

In a step 712, the balloon 123 is deflated by negative pressure on the syringe. Deflation of the balloon 123 causes the expandable cage structure 120 to collapse.

In a step 713, the catheter 110 is withdrawn from the anus.

Alternative Embodiments

Although preferred embodiments are disclosed herein, many variations are possible which remain within the concept, scope and spirit of the invention, and these variations would become clear to those skilled in the art after perusal of this application.

The invention claimed is:

1. An apparatus for heat treatment of urinary incontinence in a woman comprising:
   a catheter for insertion into a urethra and bladder; and
   an electrode-deployment structure coupled at a distal portion of said catheter, comprising:
      an expandable member that, upon expansion, deploys said at least one electrode toward a tissue targeted for treatment, allowing contact of said at least one electrode with said tissue targeted for treatment for delivery of radio frequency (RF) energy to said tissue targeted for treatment; and
   a control linkage configured to deploy said at least one electrode toward the tissue targeted for treatment.

2. The apparatus of claim 1, wherein said at least one electrode comprises four to eight electrodes.

3. The apparatus of claim 2, wherein said at least one electrode comprises four electrodes.

4. The apparatus of claim 1, further comprising a mechanical control for deploying said at least one electrode.

5. The apparatus of claim 1, further comprising an anchor configured to secure said distal portion in the urethra.

6. The apparatus of claim 1, further comprising a source of electromagnetic energy configured to 400 to 500 kilohertz.

7. The apparatus of claim 1, wherein said distal portion of said catheter comprises a tapered tip.

8. The apparatus of claim 7, wherein said tapered tip comprises at least one of:
   a flexible material; and
   a rigid material.

9. The apparatus of claim 8, wherein said catheter further comprises a source for delivering said radiofrequency energy at a frequency selected for denaturing cellular proteins.

10. The apparatus of claim 1, wherein said expandable member comprises:
    an inflatable balloon, coupled to said distal portion of said catheter.

11. The apparatus of claim 10, wherein said expandable member further comprises at least one coupled strut surrounding a central axis and having said at least one electrode coupled thereto.

12. The apparatus of claim 1, further comprising:
    lumen for cooling a tissue sample.

13. The apparatus of claim 1, further comprising:
    lumen for delivering a flowable substance, wherein said flowable substance prevents collateral thermal damage to said tissue sample.

14. A system for treating urinary incontinence in a woman, the system comprising:
    a source of RF energy; and
    a treatment catheter for insertion into a urethra and bladder neck and configured to connect to the source of RF energy, said treatment catheter having:
       an expandable electrode deployment structure coupled at a distal segment of said catheter, comprising:
          at least one electrode; and
          an expandable member that, upon expansion, deploys said at least one electrode toward a tissue targeted for treatment, allowing contact of said at least one electrode to contact said tissue targeted for treatment for delivery of radio frequency (RF) energy to said tissue targeted for treatment;
       an anchor configured to secure said distal portion in the urethra; and
       a sensor configured to feedback temperature information to regulate energy plied by the electrodes.

15. The apparatus of claim 5, wherein the anchor comprises an inflatable balloon.

16. The apparatus of claim 11, wherein said at least one coupled strut surrounds said balloon so that, upon inflation, said balloon deploys said at least one strut having said at least one electrode coupled thereto toward said tissue targeted for treatment.

17. The apparatus of claim 16, further comprising a coupling for disposal of an inflation medium within an interior space of said balloon.

18. The apparatus of claim 10, wherein said inflatable balloon comprises an anchor configured to secure said distal portion in the urethra.

* * * * *